(12) United States Patent
Hickok et al.

(10) Patent No.: US 6,976,844 B2
(45) Date of Patent: Dec. 20, 2005

(54) ULTRASONIC MICROTUBE DENTAL INSTRUMENTS AND METHODS OF USING SAME

(75) Inventors: Teresa Hickok, Bonita, CA (US); Clifford Ruddle, Santa Barbara, CA (US)

(73) Assignee: San Diego Swiss Machining, Inc., San Diego, CA (US)

(\*) Notice: Subject to any disclaimer, the term of this patent is extended or adjusted under 35 U.S.C. 154(b) by 158 days.

(21) Appl. No.: 10/413,427

(22) Filed: Apr. 14, 2003

(65) Prior Publication Data

US 2004/0126735 A1    Jul. 1, 2004

Related U.S. Application Data

(60) Provisional application No. 60/372,332, filed on Apr. 12, 2002.

(51) Int. Cl.⁷ ................................................. A61C 3/02
(52) U.S. Cl. ........................................ 433/224; 433/119
(58) Field of Search ........................ 433/118, 119, 120, 433/121, 165, 224

(56) References Cited

U.S. PATENT DOCUMENTS

| | | | |
|---|---|---|---|
| 4,832,683 A * | 5/1989 | Idemoto et al. ............... 604/22 |
| 5,085,586 A * | 2/1992 | Johnson ...................... 433/224 |
| 5,879,160 A | 3/1999 | Ruddle ....................... 433/224 |
| 5,951,286 A | 9/1999 | Rhodes ....................... 433/165 |
| 6,227,855 B1 | 5/2001 | Hickok et al. ............. 433/141 |
| 6,280,197 B1 * | 8/2001 | Benado ....................... 433/224 |
| 2003/0124485 A1 * | 7/2003 | Teraushi ..................... 433/141 |

\* cited by examiner

Primary Examiner—Cary E. O'Connor
(74) Attorney, Agent, or Firm—Lewis, Rice & Fingersh, L.C.

(57) ABSTRACT

Systems and methods related to ultrasonic microtube dental instruments designed to cut around a broken instrument by allowing the broken instrument to be placed within a lumen of the microtube instrument while simultaneously boring with the broken instrument and being guided by the broken instrument.

10 Claims, 7 Drawing Sheets

ULTRASONIC MICROTUBE DENTAL INSTRUMENTS AND METHODS OF USING SAME

CROSS REFERENCE TO RELATED APPLICATIONS

This application claims priority to U.S. Provisional Patent Application Ser. No. 60/372,332 filed Apr. 12, 2002 the entire disclosure of which is herein incorporated by reference.

BACKGROUND

1. Field of the Invention

This disclosure relates to the field of dental instruments. In particular, to ultrasonic microtube dental instruments designed to remove the remnants of broken instruments from teeth.

2. Brief Description of the Related Art

During root canal preparation procedures, the potential for instrument breakage is always present. When an instrument breaks during the procedure, the clinician is generally left with two options, attempt to remove the broken instrument, or leave the broken instrument in place and bypass the broken instrument while continuing the procedure.

Historically, the consequences of leaving and/or bypassing broken instruments have been discussed in dental literature and can be serious. In some cases, leaving the broken instrument in the tooth can necessitate extraction of the tooth in the future resulting in a loss of any benefit obtained from performing the root canal procedure in the first place.

It is therefore generally preferred that the broken instrument be removed from the tooth to prevent additional problems down the road. Historically, retrieving broken instruments posed formidable challenges. In particular, most broken instruments were files, drills, bores, or other cutting instruments that broke because of becoming wedged inside the structure of the tooth. Therefore, the very fact that the instrument was broken generally indicated that the instrument had become stuck in the tooth structure and could not be easily pulled free. Further, the instrument would often break at a point not easily visible or accessible to the clinician as a drill or similar instrument could break at a point within its own hole and therefore can not be accessed by an instrument larger than it itself without boring out additional space.

Generally, to be able to carry out an instrument retrieval, a clinician needs to open space around at least a portion of the broken instrument. In this way, another instrument which can interact on the broken instrument can be brought into contact with the broken instrument so as to allow the broken instrument to be removed. For instance, a pulling device can be placed in contact with an end of the broken instrument to allow for the broken instrument to be pulled free. Alternatively, an instrument may be used that attempts to rotate the broken instrument backwards and essentially unscrew it from the obstruction it encountered. In still further situations, as structure is removed from around the broken instrument, the structure causing the wedge may be destroyed freeing the broken instrument.

Traditionally, small files were used in efforts to either bypass or eliminate the broken instrument. As time has passed and technologies improved, retrieval techniques have evolved but are still oftentimes ineffective because of limited vision and/or restricted space. Because of the need to access the instrument and visualize the correction, efforts directed toward instrument retrieval, even when successful, often weaken roots due to overzealous canal enlargement, which in turn predisposes them to subsequent fracture and the loss of a tooth. Indeed, the prognosis of a tooth is seriously compromised if the efforts to remove a broken instrument lead to iatrogenic events, such as a ledged canal or root perforation. In these situations, the tooth is again often lost and the purpose of the procedure was compromised by the broken instrument.

Because of these types of issues, the greatest challenge to removing broken instruments is to remove them safely without unnecessarily compromising the remaining tooth structure. A variety of different instruments, devices and resulting techniques have been advocated to remove broken instruments. Newer methods to remove broken instruments require drilling to expose the proximal (broken) end of the broken instrument and to allow instruments to access the proximal end. Various methods are utilized to bore around the proximal end to expose a few millimeters of the structure of a broken instrument. This end can then be acted upon by instruments for effectuating the removal by backing out or pulling the broken instrument free with a high degree of success. Methods for exposing the critical millimeters generally the include utilizing high and low speed rotary cutting burs, and manual and rotary trephines.

The problem with these methods for exposing the broken instrument is the size of the instruments and techniques employed oftentimes result in excessive loss of tooth structure during these procedures. In particular, because the instrument being used to expose the tip is generally no smaller than the broken instrument, the diameter of the removed material can be three times what it would have otherwise have been due to having to bore around the broken instrument. Further, if smaller instruments are used, there is risk that these instruments (which are much more fragile than the broken instrument was) may also break further complicating the problem. For these reasons, it is not uncommon for iatrogenic problems to occur when attempting to retrieve a broken instrument. Namely, overzealous radicular access can equate to a loss of root structure which contributes to root fracture. In other instances, deviating from the long axis of a canal while attempting to drill around can lead to a ledge or a root perforation.

SUMMARY

Because of these and other problems in the art, disclosed herein, among other things, are ultrasonic microtube dental instruments designed to cut around a broken instrument by allowing the broken instrument to be placed within a lumen of the microtube instrument while simultaneously boring around all sides with an external cutting edge of the microtube instrument. In this way the amount of tooth structure which needs to be removed to expose enough of the broken instrument to allow removal is decreased. Further, the microtube instrument is often a stronger boring instrument.

DESCRIPTION OF PREFERRED EMBODIMENT(S)

While the embodiments described herein relate specifically to microtube instruments designed to remove broken instruments from the root canal of a human tooth, one of ordinary skill in the art would understand that the systems, methods, and mechanisms discussed herein could be readily adapted for use in other dental operations.

Further, for the purposes of this disclosure, the invention will be referred to as removing broken instruments. It should be recognized that generally only a portion of the broken instrument will need to be removed, as other portions will have come out freely after the breakage. Therefore, when a broken instrument is referred to, it is principally that portion of the instrument which needs to be removed which is being referenced. Further, while the most commonly broken instruments are files and other boring tools, the microtube instruments and methods of this invention could be used to remove any type of broken instrument including, but is not limited to, separated files, silver points, lentulos, Gates Glidden drills, carrier-based obturators, or any other dental instrument located inside the canal or otherwise wedged in the tooth. Further, the microtube instrument could be used to bore around any structure capable of fitting within the lumen even if it is not a broken instrument. For instance, a microtube instrument could be used to bore around an undamaged instrument, a guide wire, a natural portion of the tooth, or any other structure.

Figure 1:
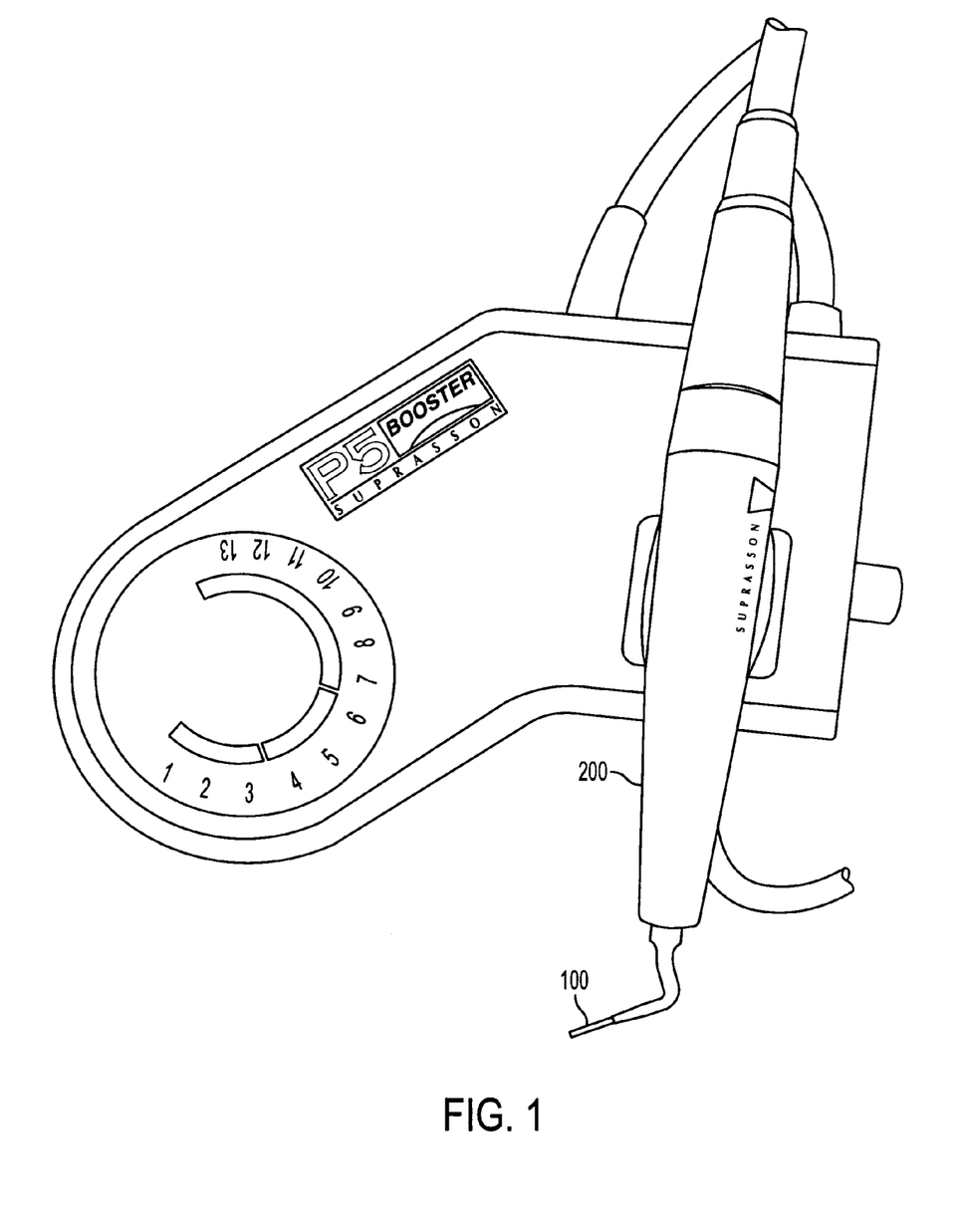
FIG. 1 provides an embodiment of a microtube instrument attached to an ultrasonic transducer.

Referring to FIG. 1 of the drawings there is illustrated an exemplary embodiment of a microtube instrument (100), in accordance with the present invention. The instrument (100) is shown connected to an ultrasonic generator (200) such as an ultrasonic vibrator or transducer of generally well-known conventional construction. In this configuration, the microtube instrument (100) would be ready for use and the clinician would place the microtube instrument (100) within the intended operating position and then activate the ultrasonic generator to use the microtube instrument (100).

As the operation and construction of ultrasonic generators is well known to those of ordinary skill in the art, this disclosure will instead focus on the microtube instrument (100) and the remaining pictures show the microtube instrument (100) separated from the ultrasonic generator (200).

Figure 2:
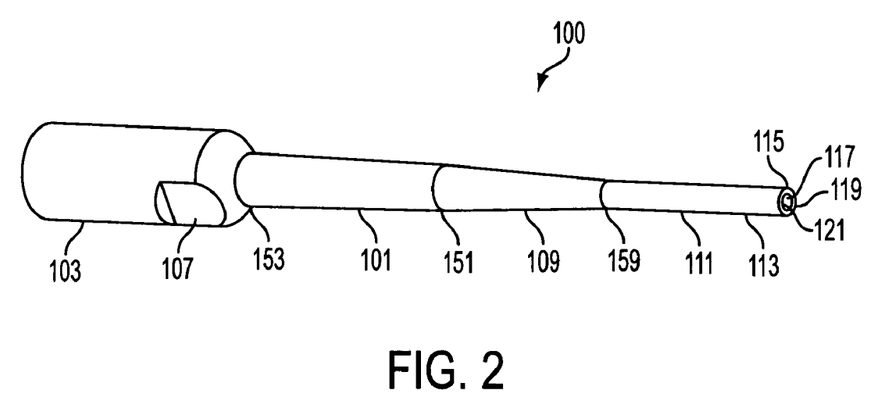
FIG. 2 provides for a perspective view of an embodiment of a straight microtube instrument.
Figure 3:
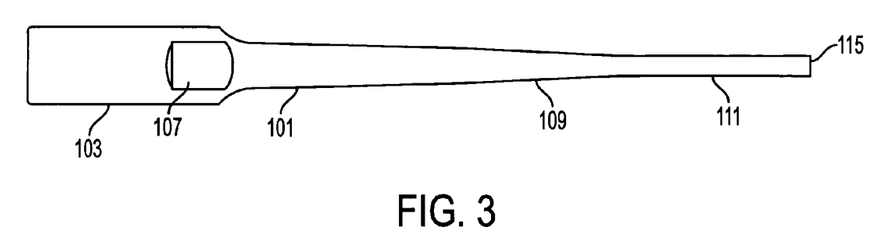
FIG. 3 provides for a side view of the embodiment of FIG. 2.
Figure 4:
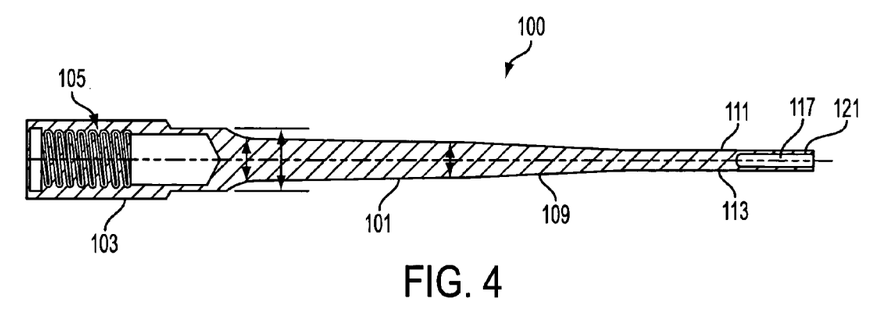
FIG. 4 provides for a cross-sectional view of the embodiment of FIG. 2.

A first embodiment of the microtube instrument (100), is illustrated in FIGS. 2–4. This is a straight microtube instrument (100). The microtube instrument (100) generally comprises an elongated shank (101), which may be of any elongated form but is preferably of generally cylindrical shape with a relatively constant diameter. Towards the proximal end (153) of the elongated shank (101) there is attached a connector (103). The connector (103) in these figures comprises an internally threaded socket (105) for threadably mounting on the end of a shaft (generally on the ultrasonic generator (200)). The connector (103) further includes at least one flat outer surface (107). In another embodiment, the entire outer surface is composed of a plurality of flat surfaces. The flat outer surface (107) provides a place for engagement by a wrench or the like for threadably tightening and loosening the microtube instrument (100) from the ultrasonic generator (200). The connector (103) may be separable from the microtube instrument (100), or may be a permanently attached to a portion thereof depending on the particular embodiment.

Towards the distal end (151) of the shank (101) there is attached an intermediate portion (109) where the shank (101) tapers gradually down to a working portion (111) attached by its proximate end (159). In other embodiments, the intermediate portion (109) may be of any shape or may be eliminated entirely with the working portion (111) connected directly to the shank (101) at its proximal end (159). The working portion (111) may be of any elongated shape but is preferably generally cylindrical and will generally be of a smaller diameter than the diameter of the shank. (101).

Figure 8:
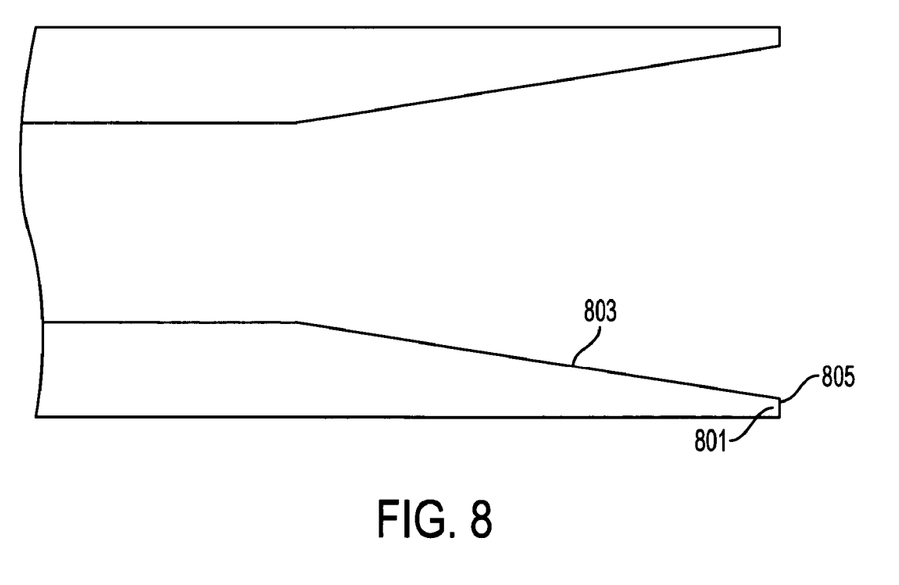
FIG. 8 provides a cross-sectional detail view of an embodiment of the cutting surface.

The working portion (111) includes two structures which together provide for the instruments working ability. On the distal end (115) of the working portion (111) adjacent the entrance to the lumen (117) there will generally be provided a cutting, filing or rasping surface designed to remove tooth structure. This cutting surface (119) may be any type of cutting surface, comprised of any material known to those of ordinary skill in the art. This includes but is not limited to, smooth (knife) edge cutting surfaces, serrated cutting surfaces, saw-t0tthed cutting surfaces, abrasive surfaces, or any other surface or combination of surfaces. Further, the cutting surface (119) may continue onto the major surface (113) of the work portion (111) any distance along the working portion (111) (or beyond) as desired and may be constructed as an integral portion of the working portion (111) or may be added on the surface thereof as a coating. FIG. 8 provides a detail view of an embodiment of the cutting surface (119) whereby the cutting surface is a sharp edge (801), formed by forming the entrance of the lumen with an angled edge (803) which approaches and may or may not reach a point at the end (805).

The working portion (111) also includes a lumen (117) which is contained within the major surface (113) of the working portion (111) giving the working portion (111) a generally hollow structure. The lumen (117) will generally extend through the distal end (115) a predetermined distance into the working portion (111) and/or intermediate portion (109). The lumen (117) is also preferably of generally cylindrical shape leading to the outer wall (121) of the working portion (111) having a generally fixed thickness without any openings therethrough. In another embodiment, however, the lumen (117) may be of a non-regular shape leading to the outer wall (121) having a varying thickness.

The depth of the lumen (117) into the working portion (111) will generally depend on the length of the working portion (111), the desired cutting depth available to the microtube instrument (100), and/or the intended use of the microtube instrument (100). It is preferred that the distance be about 5 to about 30 millimeters for most applications, but that is by no means required and a wide variety of different depths can be used. In another embodiment, the lumen (117) may extend into the intermediate portion (109), the shank (101), or entirely through the entire structure of the microtube tool (100). The diameter and/or cross-sectional shape of the lumen (117) can also depend on similar factors. As the lumen (117) will generally be placed over the broken end of a broken instrument, the cross-sectional area of the lumen (117) may vary widely to allow a wide selection of devices to fit within the lumen (117). The cross-sectional diameter of a generally cylindrical lumen will preferably be about 0.1 to about 2.0 millimeters, but that is by no means required.

From the prior discussion, it should be seen that a wide variety of differently dimensioned instruments may be created depending on the cross-sectional area of the lumen (117), the desired thickness of the outer wall (121), the depth of the lumen (117), and the length of the working portion (111). It should be recognized, that when the microtube instrument (100) is used to cut downward into a structure, generally the microtube instrument (100) will cut a circle with dimensions generally matching those of the outer wall (121) to a depth no deeper than that of the lumen (117). Further, because the lumen (117) extends through the distal end (115) the cutting action of the microtube instrument will leave a disk or pillar which is not bored but will instead enter the lumen (117).

Figure 5:
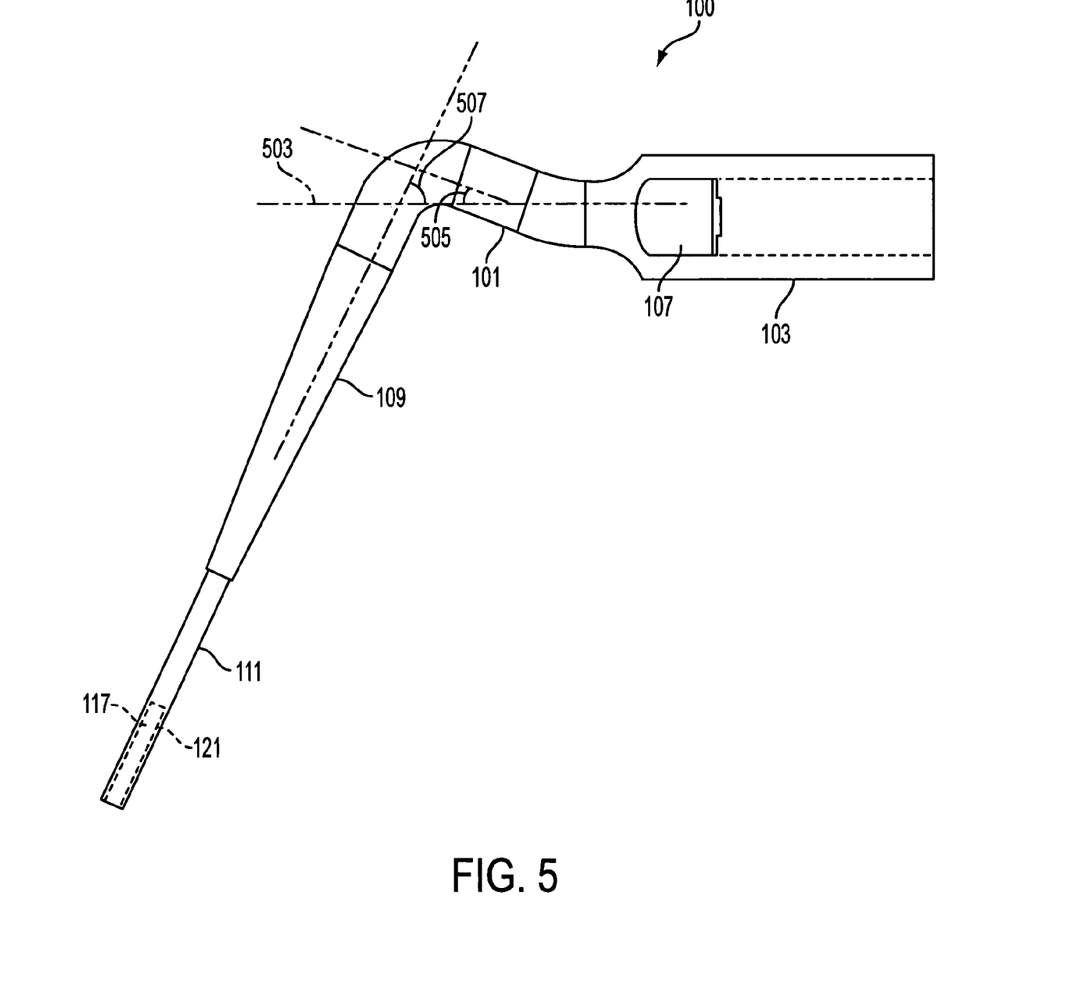
FIG. 5 provides a side view of an embodiment of a contra-angled microtube instrument.
Figure 6:
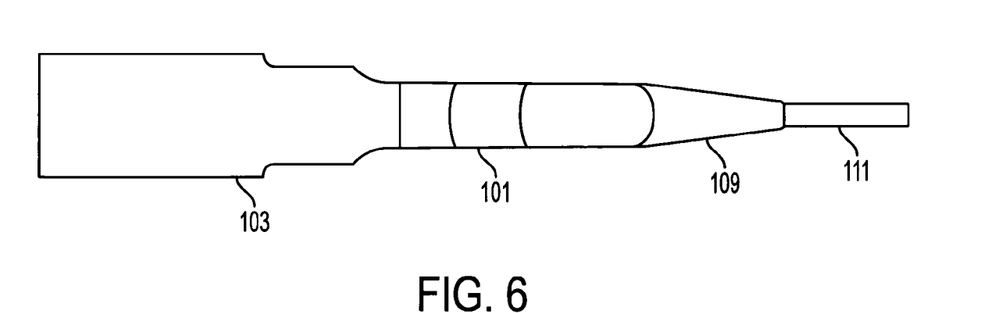
FIG. 6 provides a top view of the instrument of FIG. 5.

FIGS. 5–6 provide for a second embodiment of a microtube instrument (100) that provides an additional modification to the instrument shown in FIGS. 2–4. In this embodiment, the shank (101) is bent at an angle beyond the connector (103). While any type of angle maybe used it is preferred that the shank (101) be bent into a contra-angle. A contra-angle portion actually comprises two separate angles as the shank (101) is first curved or bent in a first direction away from the original axis of the shank (101), and is then bent back across the same axis. It is preferred, but by no means required, that the first bend forms an angle (505) of about 15 degrees to about 25 degrees with the original axis (503) and the second bend forms an angle (507) of about 45 degrees to about 70 degrees to the same axis (505) as shown in FIG. 5. The contra-angle will generally occur prior to the intermediate section (109), if one is present, but that is also not required.

The various embodiments of instruments shown in FIGS. 1–6 generally illustrate a device which can be used to cut around an existing elongate structure, without cutting into the elongate structure, so long as the elongate structure has a cross-sectional area equal to or less than the cross-sectional area of the lumen (117). Most broken instruments will generally have an elongate structure. Therefore the microtube instrument (100) can be used to bore around a broken instrument by placing the broken instrument in the lumen (117). Further, if the cross-sectional area of the lumen (117) and the broken instrument are relatively similar, the microtube instrument (100) will bore quite close to the broken instrument exposing at least a portion of its structure. Finally, because the microtube instrument (100) bores a circle about the broken instrument, the space which needs to be bored out around the broken instrument is generally less than it would be if another cutting instrument was used to bore out around the outside of the broken instrument. In particular, the microtube instrument (100) requires boring a hole of a diameter equal to the microtube working portion (111). This is often about one third the amount of space required to bore around the broken instrument of a bore with identical cross-section but lacking a lumen (117)

Figure 7:
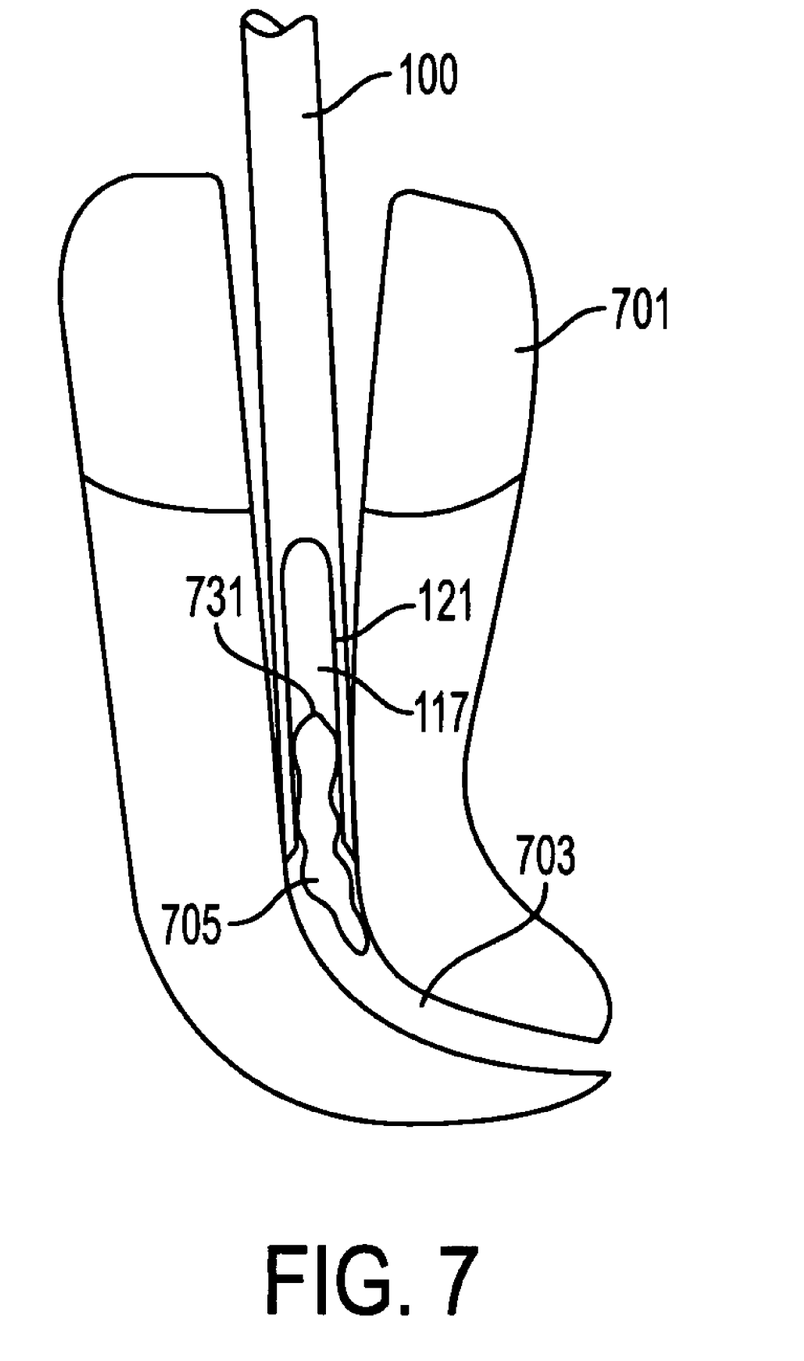
FIG. 7 provides a cross-sectional view of the tip of an embodiment of a microtube instrument as it would appear when drilling around a broken instrument in a tooth.

FIG. 7 provides for a general drawing showing how an embodiment of a microtube instrument (100) may be used to bore out a broken instrument (705). In particular, in FIG. 7 there is shown a tooth (701) having a root canal (703). Within the root canal (703) there is provided a broken instrument (705). The proximal end (731) of the broken instrument (705) is within the lumen (117) and the microtube instrument (100) is boring a circle around the broken instrument (705).

While FIG. 7 provides for a general indication of how the microtube instrument (100) works when it has been placed over the broken instrument (705), the actual procedure for getting the microtube instrument (100) into contact with the broken instrument (705) may require many more steps. In particular, to remove the broken instrument (705), several factors need to be appreciated. In particular the cross-sectional diameter, length, and curvature of the canal and the root morphology, including the cross-sectional thickness of dentia and the depth of eternal concavities. In general, if one-third of the overall length of a broken instrument (705) can be exposed, it can usually be removed. Further, broken instruments (705) that lie in the straight-away portions of the canal can usually be removed. Broken instruments (705) that lie partially around the canal curvature, although more difficult, can oftentimes be removed if straight-line access can be established to their most proximal end (731). The type of material comprising the broken instrument (705) is another important factor to be considered. Additionally, it is also useful to know if the broken instrument's (705) cutting action was clockwise versus counterclockwise before commencing with removal efforts.

Access to the proximal end (731) of the broken instrument (705) is the first step in the removal of a broken instrument (705). High-speed, friction grip, surgical length burs are selected to create straight-line access to all canal orifices. Radicular access is the second step required in the successful removal of a broken instrument (705). If radicular access is limited, hand files are usually used serially small to large, coronal to the broken instrument (705), to create sufficient space to safely introduce GG drills. These drills are then used like "brushes" to create additional space and maximize visibility above the broken instrument (705). Increasingly larger GG's are uniformly stepped out of the canal to create a smooth flowing funnel which is largest at the orifice and narrowest at the proximal end (731) of the broken instrument (705).

Once a suitable work area has been established, The clinician utilizes an embodiment of a microtube instrument (100) to circumferentially expose a short section of the broken instrument (705) (generally about 2–3 mm)

Generally, a clinician will be supplied with a kit of microtube instruments (100) having a variety of instruments scaled for the size of the working area, the tooth, and the broken instrument (705) to be removed. The microtube instruments (100) in this kit will generally have a working portion (111) ranging between 5–30 mm in length, and the lumens (117) will generally have internal diameters that can fit over a variety of different intracanal obstructions ranging from approximately 0.10 mm to 2.00 mm in diameter. Further, microtube instruments (100) in the kit may be made from a variety of different materials including, but not limited to, stainless steel, nickel titanium, titanium, or plastics for different applications.

The appropriate microtube instrument (100) for the particular situation is selected having a size and shape sufficient to reach the broken instrument (705) and pass the proximal end (731) of the broken instrument (705) into the lumen (117), generally without significant excess space. The microtube instrument (100) is inserted into the canal and the proximal end (731) of the broken instrument (705) is directed within the lumen (117). Once the proximal end (731) is within the lumen (117), the microtube instrument (100) may be activated by the clinician. The microtube instrument (100) will then serve to bore the area surrounding the broken instrument (705), generally on all sides.

The broken instrument (705) also serves as a guide during the boring procedure. As the broken instrument (705) is within the lumen (117) the microtube instrument (100) will generally remain aligned over the broken instrument (705) following its shape to direct the microtube instrument (100)

to carve out the area surrounding the broken instrument (705), even when the portion of the broken instrument (705) being bored out is not visible. Further, because of the flexibility available to a microtube instrument (100), the microtube instrument (100) can even track broken instruments (705) that are bent or curved in their positioning, allowing for broken instruments (705) much deeper in the canal, or in much more difficult positions, to be removed.

Once a portion of the broken instrument (705) has been exposed, a removal device may be inserted to grasp and remove the broken instrument (705). Once such device which may be used is described in U.S. Pat. No. 6,227,855 the entire disclosure of which is herein incorporated by reference.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

What is claimed is:

1. A method of removing a broken instrument from a root canal of a tooth, the method comprising:
   getting an instrument, the instrument having a distal end including a cutting surface and a lumen extending from said cutting surface;
   placing said lumen over a proximal end of said broken instrument so as to place said cutting surface in contact with said tooth;
   ultrasonically driving said instrument to cut into said tooth with said cutting surface so as to loosen said broken instrument relative to said tooth; and
   removing said broken instrument.

2. The method of claim 1 wherein said instrument further includes:
   a connector configured to attach said instrument to an ultrasonic generator;
   an elongated shank attached to said connector; and
   a working portion having a length and a proximal and distal end, said working portion being attached to said elongated shank by said proximal end;
   wherein, said working portion includes said cutting surface and said lumen.

3. The method of claim 2 wherein said proximal end of said working portion is attached to an intermediate section which is in turn attached to said elongated shank.

4. The method of claim 2 wherein said working portion is generally cylindrical in shape.

5. The method of claim 2 wherein said lumen is generally cylindrical in shape.

6. The method of claim 2 wherein said shank is generally cylindrical in shape.

7. The method of claim 2 wherein said shank is straight.

8. The method of claim 2 wherein said shank is bent.

9. The method of claim 8 wherein said shank is bent into a contra-angle.

10. The method of claim 2 wherein said cutting surface is on said distal end adjacent said lumen.

* * * * *